(«United States Patent» [19]

Inoue

[11] 4,327,736
[45] May 4, 1982

[54] BALLOON CATHETER

[76] Inventor: Kanji Inoue, 2-22, Asahi-cho, Kohchi-shi, Kohchi-ken, Japan

[21] Appl. No.: 96,143

[22] Filed: Nov. 20, 1979

[51] Int. Cl.³ .............................................. A61M 25/00
[52] U.S. Cl. ................................................. 128/349 B
[58] Field of Search ..................... 128/399, 349 B, 344

[56] References Cited

U.S. PATENT DOCUMENTS

| | | | |
|---|---|---|---|
| 1,690,995 | 11/1928 | Pratt | 128/344 |
| 2,499,045 | 2/1950 | Walker et al. | 128/344 X |
| 3,045,677 | 7/1962 | Wallace | 128/349 B |
| 3,889,685 | 6/1975 | Miller, Jr. et al. | 128/349 B |

Primary Examiner—Stephen C. Pellegrino

[57] ABSTRACT

Disclosed is an improved balloon catheter having a three-layer balloon tube fixed to and enclosing an apertured end of an elongated flexible fine tube. The three-layer composite balloon tube is composed of inner and outer rubber tubes and an intervenient cloth bag, which is effective to hold the shape and size of the expanding balloon appropriately for the purpose and to raise and keep the inner-pressure of the expanding balloon at an elevated value without any fear for rupturing a hollow organ of a human body. A pair of rubber bands are dispersed about portions of the balloon to initially restrict expansion of said portions at a stenosis of the hollow organ.

1 Claim, 13 Drawing Figures

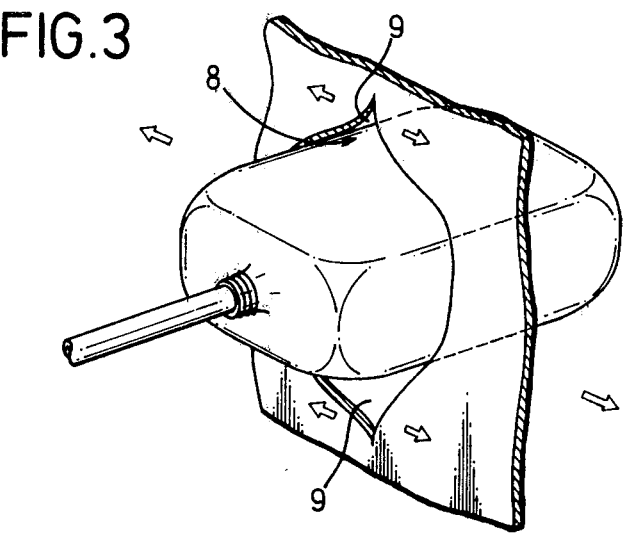
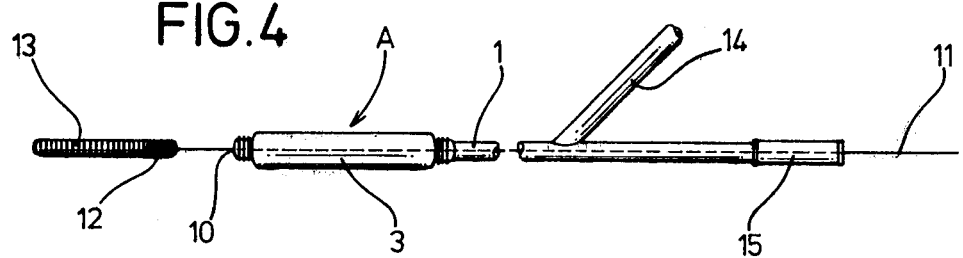
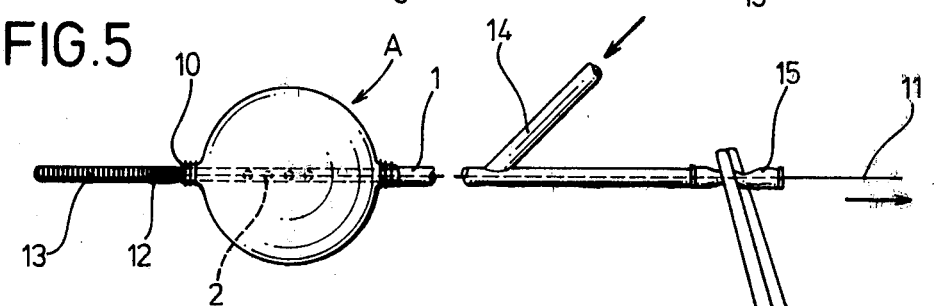
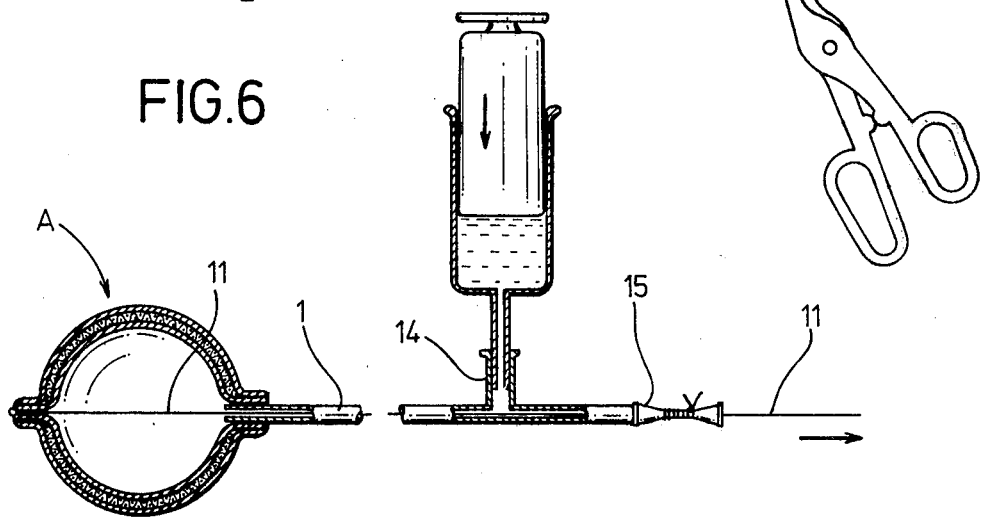

BALLOON CATHETER

DETAILED EXPLANATION OF THE INVENTION

This invention relates to an improvement of balloon catheter for medical use.

A conventional balloon catheter uses an elongated tube of soft rubber. In use a rubber tube is inserted in a hollow organ of a human body, and then a liquid such as salt water is supplied under pressure to the rubber tube, thereby causing the tube to expand in the form of balloon. The balloon catheter, however, cannot enlarge the stenosis of the hollow organ as large as desired due to a relatively low inner-pressure of the balloon. Also, there is a fear for rupturing a hollow organ by raising an inner-pressure of the balloon in the organ far beyond the normal shape and size of the balloon.

One object of this invention is to provide a balloon catheter which is capable of increasing the inner-pressure of the expanding balloon while keeping the volume of expansion at a given constant value.

Another object of this invention is to provide a balloon catheter the shape of which changes from cocoon to ball at a stenosis of a hollow organ in operation, thus assuring the enlargement of the stenosis of the hollow organ.

Still another object of this invention is to provide a balloon catheter which is capable of following a curved path to a hollow organ of a human body.

Other objects and advantages of this invention will be understood from the following description of preferred embodiments according to this invention with reference to the accompanying drawings in which:

FIG. 3 is a perspective view of a third embodiment according to this invention, showing the manner in which the square-shaped balloon expands the mitral orifice of a heart;

FIG. 4 shows the condition in which a spiral guide tip is put ahead from the ballon catheter;

FIG. 5 shows the condition in which the spiral guide tip is withdrawn to the end of the balloon catheter; and FIG. 6 shows a fourth embodiment according to this invention, which is advantageously used in inserting into a very fine blood vessel.

Figure 1:
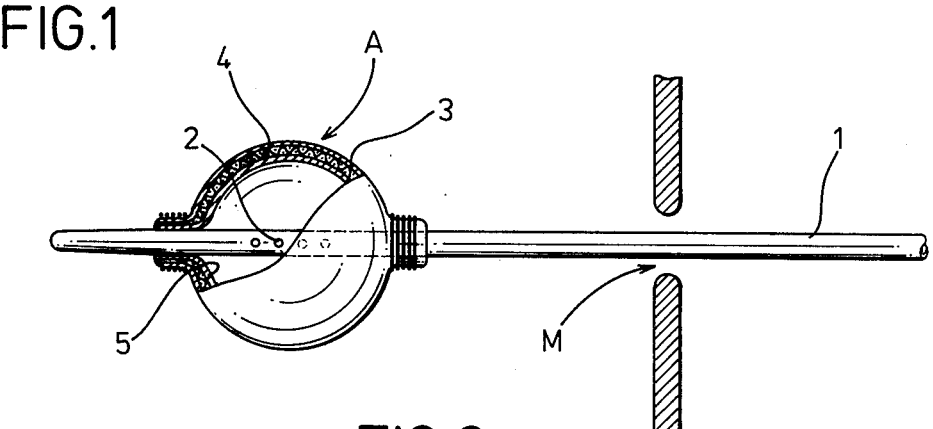
FIG. 1 shows a first embodiment according to this invention partly broken to show the inner structure of the balloon and an associated part of a flexible tube.

Referring to FIG. 1, one end part of a flexible fine tube 1 has a plurality of apertures 2. A soft rubber tube 3 which is adapted to expand into a balloon "A" in operation, is fixed to the apertured end part of the flexible tube. The outermost balloon tube 3 is lined by a cloth bag 4, which is lined by another rubber tube 5, too.

The so composed three-layer tube is tightly bound at either end to the apertured end part of the flexible fine tube, and the end is closed.

A cloth bag 4 is advantageously composed of a net bag of fine and strong strings. Such net bag is of small volume, contributing the reduction of whole size of a balloon catheter, and making it easier to insert the balloon catheter in a hollow organ of a human body.

In use a three-layer balloon tube "A" at the end of a flexible fine tube 1 is inserted in a hollow organ such as stomach through the stenosis of the organ. Then, salt water is fed from the open opposite end of the flexible tube 1 to the balloon tube "A" through the apertures 2 of the closed end part of the flexible tube 1, thus causing the inner and outer soft tubes 5 and 3 of the composite layer structure to expand along with the cloth bag 4.

The cloth bag 4 is effective to keep the physical shape and size of the balloon "A" even if the inner-pressure of the balloon is raised too high. Also, the cloth bag 4 is effective to keep the balloon at an elevated value of inner-pressure and hold it stiff.

The balloon tube is inserted in a hollow organ to expand therein. The expanding and thereby stiff balloon is withdrawn and inserted in the stenosis of the hollow organ by withdrawing the flexible fine tube 1. Then, the stenosis of the hollow organ is made to open wide.

The physical size of the expanding balloon "A" is latitudinally within the range from 17 to 30 milimeters, and is longitudinally within the range from 12 to 25 milimeters.

Referring to FIGS. 2a–2g, there is shown a second embodiment according to this invention, which is similar to the first embodiment except for a relatively broad rubber band 6 around the middle part of the cloth bag and a relatively narrow rubber band 7 around the cloth bag behind the broad one 6.

Figure 2:
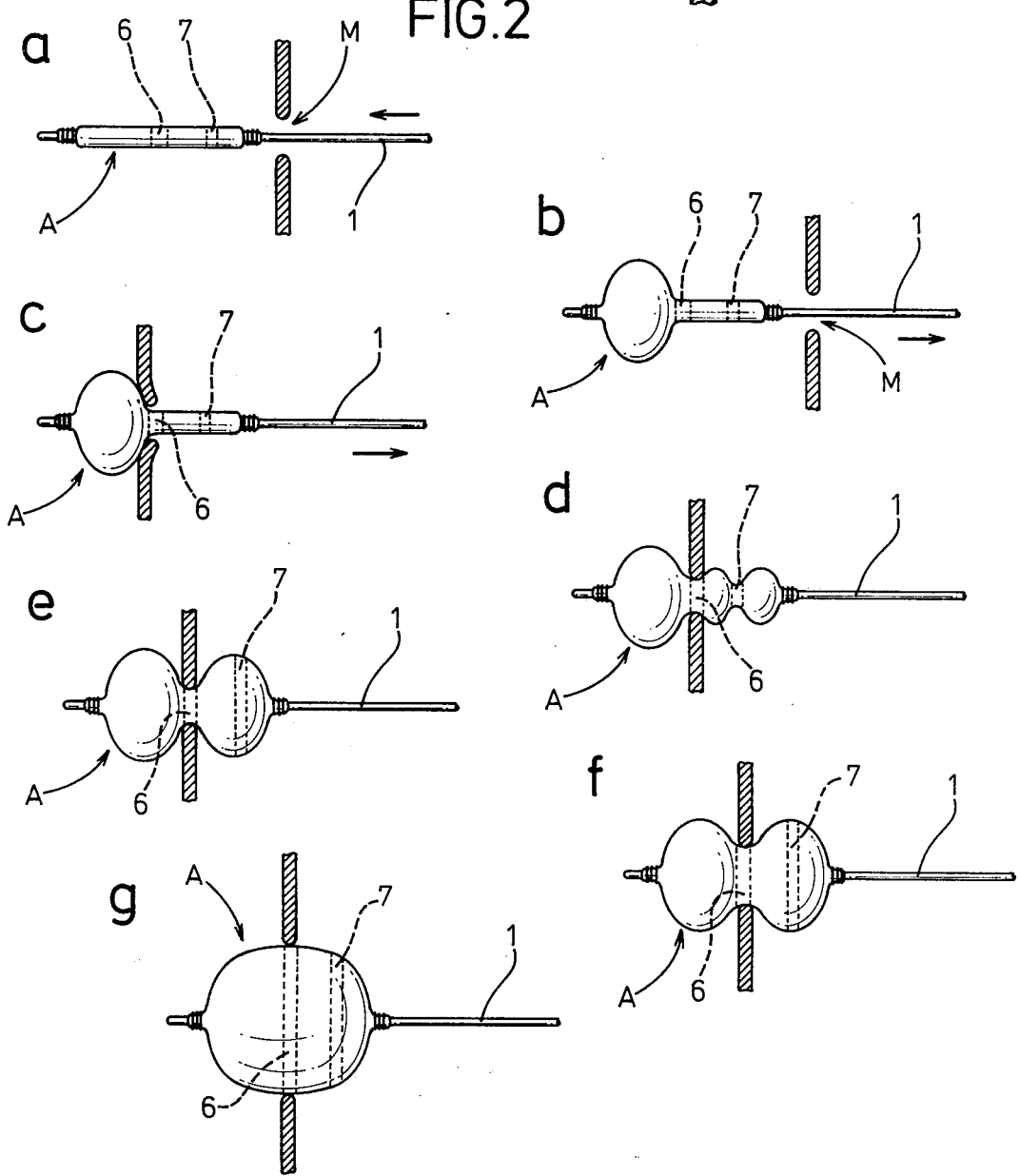
FIGS. 2a to 2g show a second embodiment according to this invention in successive steps of operation.

In operation, first, the composite balloon tube is inserted in a hollow organ through a stenosis "M" of the organ, as shown in FIG. 2a. Then, a liquid is fed to the balloon tube, thus causing the head portion of the balloon tube to expand. The rubber bands 6 and 7 prevent the tail portion of the balloon tube from expanding (See FIG. 2b). Then, the middle part of the balloon tube with the broad rubber band therearound is brought into the stenosis "M" by withdrawing the flexible fine tube 1 (See FIG. 2c).

The liquid is again fed to the balloon tube "A" through the flexible tube 1. Then, the cloth bag 4 prevents the head portion of the balloon tube "A" from further expanding, and therefore the tail portion of the balloon tube "A" starts expansion (See FIG. 2d). Partly because the middle part of the balloon tube is held under the relatively strong resilience of the broad band plus the stiffness of the stenosis of the hollow organ, and partly because the tail portion of the balloon tube is exerted by the relatively weak resilience of the narrow band, it is the tail portion of the balloon tube which starts expansion (See FIG. 2e).

As a result the middle portion of the balloon tube constitutes a neck, separating the expanding head and the expanding tail from each other, thereby preventing the balloon tube from slipping off from the stenosis "M" of the hollow organ. By increasing the inner-pressure of the balloon the middle part of the balloon tube yieldingly expands (See FIG. 2f) until the stenosis "M" of the hollow organ has been open wide (See FIG. 2g).

As is apparent from the above, in operation, the middle part of the balloon tube with the broad rubber band 6 around constitutes a neck at a stenosis of a hollow organ, separating the expanding head and the expanding tail from each other. Thus, the neck of the expanding balloon is caught by the stenosis of the balloon organ, thereby positively preventing the balloon tube from slipping off from the stenosis of the hollow organ, and by raising the inner-pressure of the balloon tube the middle part set in proper position yieldingly expands to enlarge the stenosis of the hollow organ.

Referring to FIG. 3, there is shown a third embodiment according to this invention in which a cloth bag is in the form of square. The balloon tube with wide and narrow rubber bands 6 and 7 is inserted in the mitral value of a heart through a jugular vein. The middle part of the balloon tube is put at the mitral orifice 8 of the mitral value, and then it expands in the form of square box, thereby making the commissure 9 of the mitral orifice open wide as indicated by arrow in FIG. 3. This made of square opening is advantageous to the medical treatment of the mitral stenosis.

The expanding square balloon are preferably 30 milimeters long and 18 milimeters wide, and the balloon tube prior to expansion is 18 milimeters thick.

The second and third embodiments are described as having two wide and narrow rubber bands around the cloth bag. It, however, suffices that the cloth bag has a single rubber band around the rear part of the bag. In operation, first, the head part of the balloon tube expands to the shape and size which is limited by the cloth bag. Then, the fine tube is withdrawn so that the expanding head part is caught by the stenosis of a hollow organ. In this position the rear part of the balloon tube is made to expand, thereby constituting a neck portion around the single band. The liquid under pressure is fed to the expanding tail part to cause the single rubber band to yieldingly expand and open the stenosis of the hollow organ wide. This single band around the rear part of the balloon tube may be of a single thread which is easy to be broken. Then, after expansion of the head part of the balloon tube, the thread is broken so as to enlarge the stenosis of the hollow organ. A balloon catheter having a cloth bag bound a single thread cannot be reused. This disposable balloon catheter is advantageously thin and smooth at the balloon tube thereof, compared with the one having two rubber bands, and therefore it can be easily applied to small hollow organs.

Referring to FIGS. 4 and 5, there is shown a fourth embodiment according to this invention. As shown, a balloon catheter has a flexible fine tube 1 opening at the apertured end part 10 of the tube. A three-layer composite tube which consists of inner and outer soft rubber tubes 3 and 5 and an intermediate cloth bag 4, is tightly bound to the apertured end part. The other end of the flexible fine tube 1 has a branch tube 14. A length of operating wire 11 is inserted in the flexible tube until the end of the operating wire has appeared at the open opposite end of the fine tube 1. A plug 12 and a flexible spiral spring 13 are fixed to the end of the operating rod in the order named.

As shown in FIG. 4, the balloon catheter with the plug 12 ahead of the open end of the fine tube 1 is driven, allowing the spiral spring 13 to yieldingly follow a curved path and guide the following balloon tube to a hollow organ. Otherwise, the operating wire 11 alone is pushed to advance on the way to a hollow organ until it has reached the hollow organ, and then the fine tube 1 is driven along the extension of the operating wire to the hollow organ.

When the balloon tube has passed through the stenosis of a hollow organ, the operating wire 11 is pulled behind, thus causing the plug 12 to close the open front end 10 of the fine tube 1. Then, a rubber end tube 15 which is fitted in the rear end of the fine tube is pinched off by a clamp as shown in FIG. 5. Salt water is fed to the balloon tube from the branch tube 14, thereby causing the balloon tube "A" to expand.

Then, the fine tube 1 is pulled behind, thereby causing the expanding balloon "A" to enlarge the stenosis of the hollow organ.

A balloon catheter according to this invention has a three-layer balloon tube consisting of inner and outer rubber tubes 3 and 5 and an intermediate cloth bag 4, and therefore it is thicker than a conventional single layer balloon catheter. The thickness of the balloon tube is not significant, causing no adverse effect at all. The guiding tip of flexible spiral spring, however, is most effective to allow the balloon tube to smoothly follow a curved path to a hollow organ of a human body. Also, the open opposite end of the fine tube 1 can be easily closed simply by pulling the operating wire behind, and at the same time the open end of the fine tube can be closed so as to put the balloon catheter ready to expand.

Referring to FIG. 6, there is shown a fourth embodiment according to this invention. As shown, a three-layer balloon tube "A" is fixed to the open head end of a fine flexible tube 1. A length of wire 11 extends from the branched tail end to the open head end, and the tip of the operating wire 11 is fixed to the balloon tube. In operation the operating wire is pushed ahead to stretch the balloon in the form of elongated tube, thus making it easy to insert the balloon catheter in a very fine blood vessel. After the so-stretched balloon has reached the stenosis of a hollow organ, the operating wire is somewhat pulled behind so as to loosen the balloon.

Then, the open tail end of the flexible tube 1 is closed by binding and pinching with thread or by pinching with a clamp. Finally salt water is supplied from the branch 14 of the tail end of the flexible tube, thus expanding the balloon "A" to the full capacity.

What is claimed is

1. A balloon catheter comprising a flexible fine tube having a closed apertured end portion; and a composite balloon tube comprising outer and inner expandable rubber tubes and an intermediate cloth bag limiting the expansion of said outer and inner tubes, the opposite ends of said balloon tube being affixed to the end portions of said flexible fine tube, a relatively wide rubber band disposed around and at about the middle part of said composite balloon tube to initially restrict the expansion of said composite balloon at about the stenosis of a body cavity upon inflation of said composite balloon tube, and a relatively narrow rubber band disposed around a portion of said composite balloon tube outside of said stenosis to initially restrict the expansion of said composite balloon outside of said stenosis, so that upon insertion of the composite balloon tube and inflation thereof, said tube will become inflated first within said stenosis, then outside of said stenosis, and finally between both the inside and outside of said stenosis to enlarge the same.

* * * * *